(12) United States Patent
Green et al.

(10) Patent No.: US 8,235,256 B2
(45) Date of Patent: Aug. 7, 2012

(54) MANUAL PUMP MECHANISM AND DELIVERY SYSTEM

(75) Inventors: Lawrence Green, Santa Ana, CA (US); Arturo A. Gonzalez, Fullerton, CA (US)

(73) Assignee: Kyphon Sarl, Dallas, TX (US)

( * ) Notice: Subject to any disclaimer, the term of this patent is extended or adjusted under 35 U.S.C. 154(b) by 814 days.

(21) Appl. No.: 10/776,209

(22) Filed: Feb. 12, 2004

(65) Prior Publication Data

US 2005/0180806 A1     Aug. 18, 2005

(51) Int. Cl.
*B67D 3/00* (2006.01)
(52) U.S. Cl. ........ 222/389; 222/324; 222/527; 600/432; 604/150; 604/181
(58) Field of Classification Search .................. 222/389, 222/324, 527; 285/341, 343; 600/432; 604/146, 604/97.03, 150, 181
See application file for complete search history.

(56) References Cited

U.S. PATENT DOCUMENTS

| | | | | |
|---|---|---|---|---|
| 2,299,492 A | * | 10/1942 | Pfauser | 222/318 |
| 3,279,660 A | * | 10/1966 | Collar | 222/397 |
| 4,231,494 A | | 11/1980 | Greenwood | |
| 4,250,887 A | * | 2/1981 | Dardik et al. | 600/432 |
| 4,522,621 A | * | 6/1985 | Cassou | 604/140 |
| 4,723,479 A | * | 2/1988 | Gallentine | 92/6 R |
| 4,776,618 A | * | 10/1988 | Barree | 285/341 |
| 4,823,588 A | * | 4/1989 | Bussereau et al. | 72/453.06 |
| 4,854,482 A | * | 8/1989 | Bergner | 222/94 |
| 5,015,233 A | * | 5/1991 | McGough et al. | 604/97.03 |
| 5,254,092 A | | 10/1993 | Polyak | |
| 5,411,180 A | | 5/1995 | Dumelle et al. | |
| 5,573,265 A | | 11/1996 | Pradel et al. | |
| 6,041,977 A | | 3/2000 | Lisi | |
| 6,074,582 A | | 6/2000 | Jacino | |
| 6,267,999 B1 | | 7/2001 | Romer | |
| 6,494,345 B2 | | 12/2002 | Schrader | |
| 6,575,331 B1 | * | 6/2003 | Peeler et al. | 222/1 |
| 6,662,969 B2 | * | 12/2003 | Peeler et al. | 222/1 |
| 7,008,433 B2 | | 3/2006 | Voellmicke | |
| 2003/0111487 A1 | | 6/2003 | Peeler | |
| 2003/0216692 A1 | * | 11/2003 | Fago et al. | 604/150 |
| 2005/0070915 A1 | | 3/2005 | Mazzuca | |
| 2006/0074433 A1 | | 4/2006 | McGill | |
| 2006/0264967 A1 | | 11/2006 | Ferreyro | |

FOREIGN PATENT DOCUMENTS

| | | |
|---|---|---|
| DE | 42 26 956 A1 | 2/1994 |
| FR | 1548575 | 12/1968 |
| WO | 94/07551 A1 | 4/1994 |
| WO | WO 02/064194 | 8/2002 |

OTHER PUBLICATIONS

US Search Report for US 2005/0180806.

* cited by examiner

*Primary Examiner* — Kevin P Shaver
*Assistant Examiner* — Melvin Cartagena
(74) *Attorney, Agent, or Firm* — Dilworth & Barrese (57) ABSTRACT

A system consisting of a hand-piece with a lever operated hydraulic pump and a fluid reservoir, a connecting tube and a remote connector which will seal to a syringe body which contains a viscous material. The pump expels fluid from the reservoir into the top of the syringe via the connecting tube where the fluid presses on the syringe plunger expelling the viscous material from the primary chamber of the syringe.

14 Claims, 7 Drawing Sheets

MANUAL PUMP MECHANISM AND DELIVERY SYSTEM

BACKGROUND OF THE INVENTION

1. Field of the Invention

The system is utilized in a procedure wherein a viscous material is injected into a body, in general, and to such a system wherein the injection is controlled by a remote hydraulic pressure pump, in particular.

2. Prior Art

There are certain known surgical procedures where a viscous material is injected into a body (or body part) while the injection of the material is monitored with a fluoroscope or X-ray type device. The material being injected is, typically, a thick paste or putty-like material which is difficult to force through the small tube extending from the remote syringe devices. In these procedures, the individual who activates the system, typically a surgeon, receives repetitive and prolonged exposure to radiation from the monitoring device.

Currently, several techniques are used to lower the radiation exposure of the surgeon (or other facilitator of similar procedures). In one such technique lead lined gloves are worn by the operator to reduce the effect of the radiation. However, the lead-lined gloves are heavy and clumsy to use and still require the user to be close enough to the field to be subjected to radiation scatter.

In another technique, a remote syringe body expels the fluid through a long tube which extends into the radiation field. This device leaves the syringe at the original location and uses a secondary fluid to exert the force into the radiation field. However, in the known devices the physical requirements on the user are extreme and the pressures required cause numerous failures.

SUMMARY OF THE INSTANT INVENTION

The system of the instant invention consists of a hand-piece with a lever operated hydraulic pump and a fluid reservoir, a connecting tube and a remote connector which will seal to a syringe body. The pump expels the fluid from the fluid reservoir through the connecting tube into the top of the syringe where the fluid presses on the syringe plunger thereby expelling the material contained in the primary chamber of the syringe therefrom.

By using a low viscosity, inexpensive, secondary incompressible fluid in the connecting tube, the force required to expel material from the syringe can be reduced and the volume of injection fluid, which is typically expensive, can be reduced. The use of a small hand pump allows the device to be lightweight, compact and ergonomically designed.

DESCRIPTION OF A PREFERRED EMBODIMENT

Figure 1:
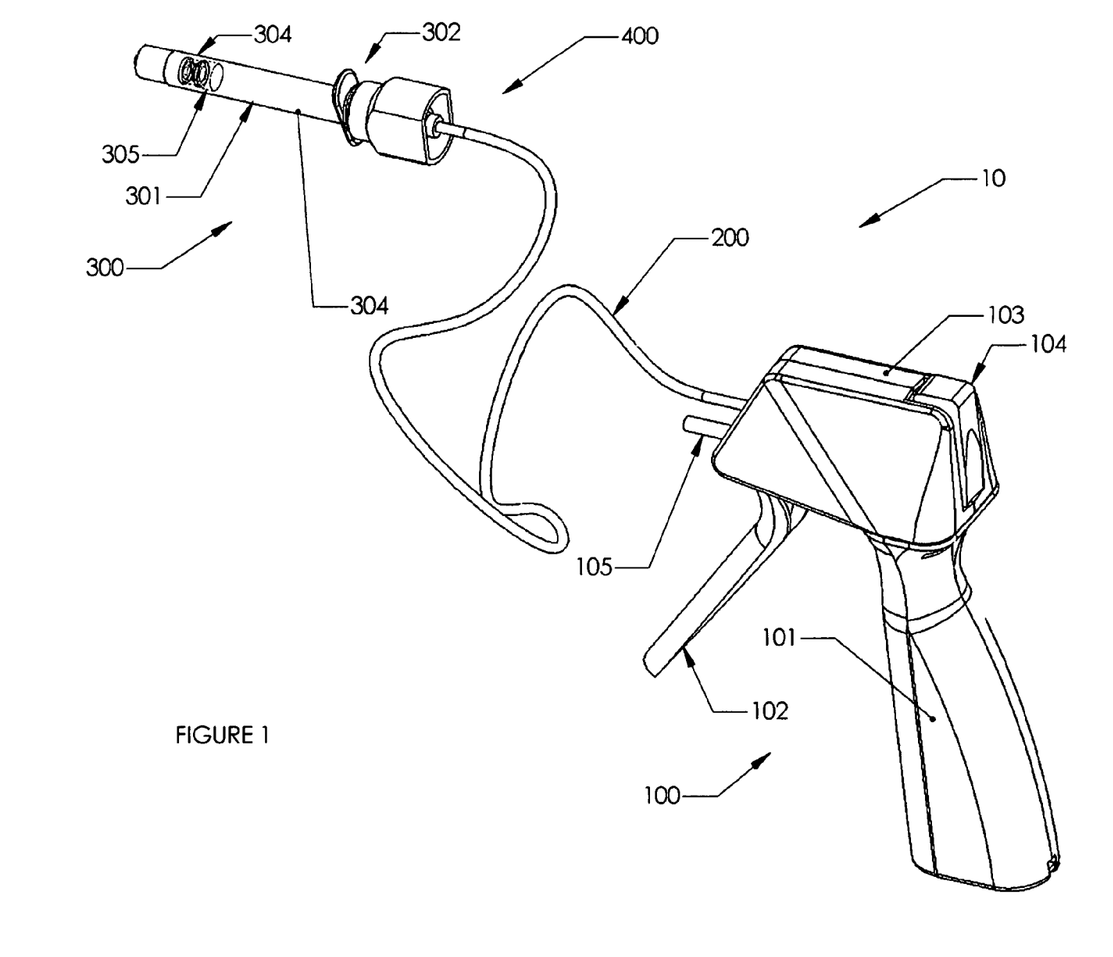
FIG. 1 is a perspective view of one embodiment of the manual pump and delivery system of the instant invention.

Referring now to FIG. 1, there is shown a perspective view of a preferred embodiment of the pump and delivery system 10 of the instant invention in the assembled status.

The pump 100 includes a pistol-grip handle 101 which is, typically, ergonomically designed for comfort of the user. A housing 103 is mounted at the upper end of handle 101. A trigger 102 is pivotally mounted within housing 103 forward of the handle 101. Typically, trigger 102 is designed to comfortably interact with the front surface of handle 101.

A pressure release valve actuator 104 is also pivotally mounted in the upper rear section of the housing 103.

A piston 105 is mounted to the trigger 102 in the forward portion of the housing 103. Piston 105 is selectively moved in and out relative to housing 103 when the trigger 102 is manipulated by the user. The motion of the piston 105 activates the pump 100 as described infra.

In a preferred embodiment, a conduit 200 comprises a hollow tube of any desired length fabricated of a flexible plastic material such as nylon. While the conduit 200 is, typically, fabricated of a transparent material, this is not a requirement of the invention. The conduit 200 is attached to the pump 100 at or within the housing 103 as described infra.

When included in the system, the conduit 200 is connected to the delivery unit 300 by means of the connector 400 for controlling the operation of the unit 300, as described infra.

The delivery unit 300 includes a syringe 301 which is, typically, a hollow cylindrical body fabricated of material such as polycarbonate which may be transparent for ease in visualizing the contents thereof. The syringe is adapted to be connected to the pump directly or via conduit 200.

Finger tabs 302 may be formed at one end of the syringe 301, if desired. The finger tabs (or any other suitable arrangement) may be utilized by the user to manipulate the syringe. A threaded connector (not visible in FIG. 1) is provided at the end of syringe 301.

Plunger 304 is disposed within the syringe 301. The plunger includes a plunger head 304 which has an outer diameter which is quite close to the inner diameter of the syringe to provide a close fit to enhance the force of the plunger on the contents of the syringe. A seal 305, similar to an O-ring or the like, is provided at the plunger head to provide a seal between the plunger and the syringe to prevent leakage around the head of the plunger 304.

Connector 400 is rotatably mounted to conduit 200 to prevent twisting or kinking of conduit 200 when the connector 400 is threadedly attached to the delivery unit 300 is described infra.

Figure 2:
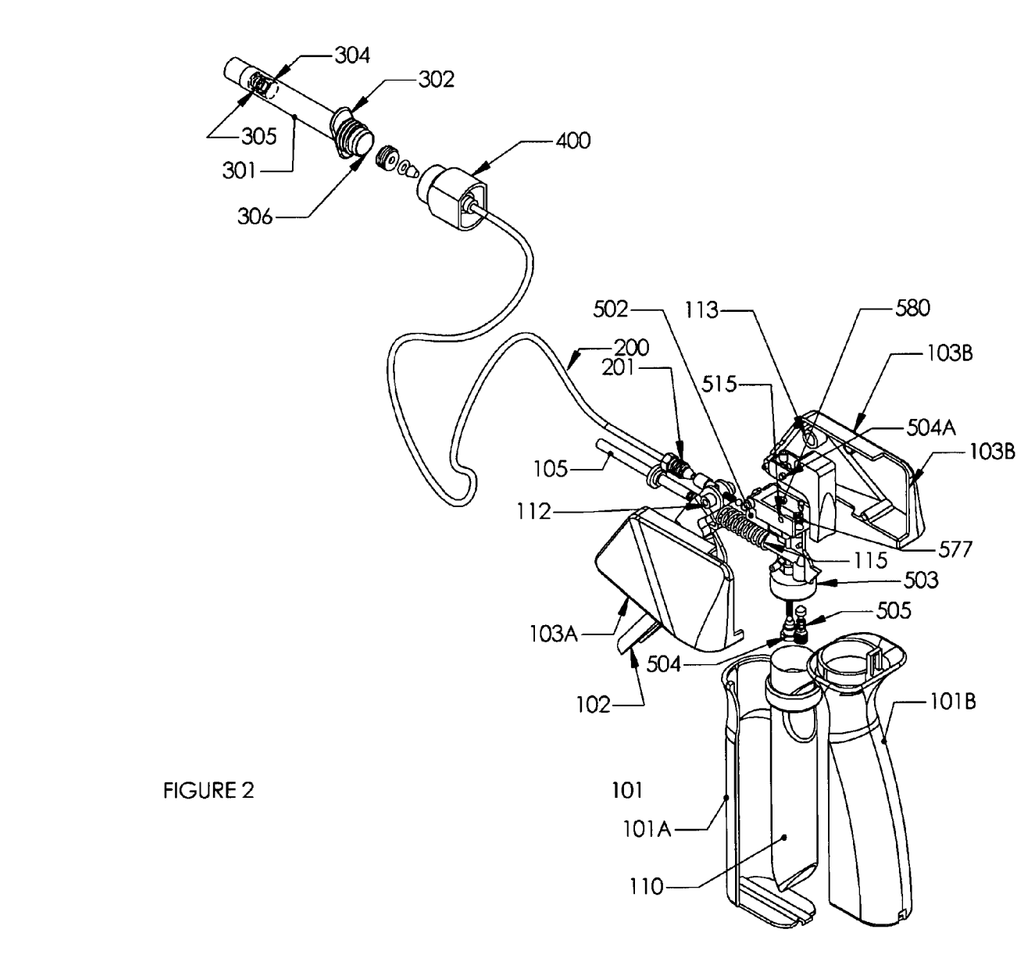
FIG. 2 is a partially broken away, exploded view of one embodiment of the manual pump and delivery system of the instant invention.

Referring now to FIG. 2, there is shown a partially exploded view of the pump and delivery system 10 of the instant invention as shown in FIG. 1.

As noted, the pump 100 includes a grip handle 101. In particular, the grip handle 101 includes the front portion 101A and the rear portion 101B which are formed of a suitable material such as white abs. The front portion 101A and the rear portion 101B are, typically, separate components which snap together to form the grip handle 101.

A suitable container 110 such as (but not limited to) a soft flexible waterproof bag is mounted in the grip handle 101.

The container 110 stores a suitable incompressible liquid such as water or the like therein.

The valve housing 103, mounted at the upper end of handle 101, includes opposing sides 103A and 103B which are formed of a suitable material such as white abs. The opposing sides 103A and 103B are, typically, separate components which snap together to form for the valve housing 103 which supports the trigger 102 and the valve mechanism body 500. The manual pressure release valve actuator 104, the piston 105 and the connection 201 for conduit 200 are supported by the valve mechanism body 500.

A piston 105 is mounted to the trigger 102 in the forward portion of the housing 103. Piston 105 is selectively moved in and out relative to housing 103 when the trigger 102 is manipulated by the user. The motion of the piston 105 activates the pump 100 as described infra.

Piston 105 is, selectively, driven into chamber 503 (in the valve mechanism body 500) by applying pressure to trigger 102 which rotates on pins 112 which are rotatably mounted in hub 113 formed on the interior of opposing sides 103A and 103B of housing 103. Spring 115 is mounted in the valve mechanism 500 and spring loads the piston 105 and the handle 102 to return to the position shown in FIGS. 1, 2 and 3.

The chamber 503 communicates with check valves 504, 505 and 506 (described infra) to selectively transfer the liquid stored in container 110 to the conduit 200 which is connected to chamber 507 (which contains check valve 551).

The manual pressure release valve actuator 104 is pivotally mounted in the support bracket 515 by pins 504A in slots 515A. A ball valve 580 is selectively released by rotation of the valve handle 104 around the pins 504A which opens a release valve in valve mechanism body 500.

The end 306 of syringe 301 is threaded for attachment to the rotating air bleed connector 400 which is rotatably connected to the end of conduit 200.

Conduit 200 comprises a hollow tube fabricated of a flexible plastic material such as nylon. While the conduit 200 is, typically, fabricated of a transparent material, this is not a requirement of the invention. The conduit 200 is attached to the body 500 within the housing 103 as described infra.

The conduit 200 is connected to the delivery unit 300 by means of the connector 400 for controlling the operation of the unit 300, as described infra.

The delivery unit 300 includes a hollow syringe 301 which is, typically, fabricated of transparent material for ease in visualizing the contents thereof. Finger tabs 302 are formed at one end of the syringe 301. The finger tabs are utilized by the user to manipulate the syringe.

Plunger 303 is disposed within the syringe 301. The plunger includes a plunger head 304 which has an outer diameter which is quite close to the inner diameter of the syringe to provide a close fit to enhance the force of the plunger on the contents of the syringe. A seal 305 similar to an O-ring or the like is provided at the plunger head to provide a seal between the plunger and the syringe to prevent leakage around the plunger head 304.

Connector 400 is rotatably mounted to conduit 200 to prevent twisting or kinking of conduit 200 when the connector 400 is threadedly attached to the delivery unit 300.

Figure 3:
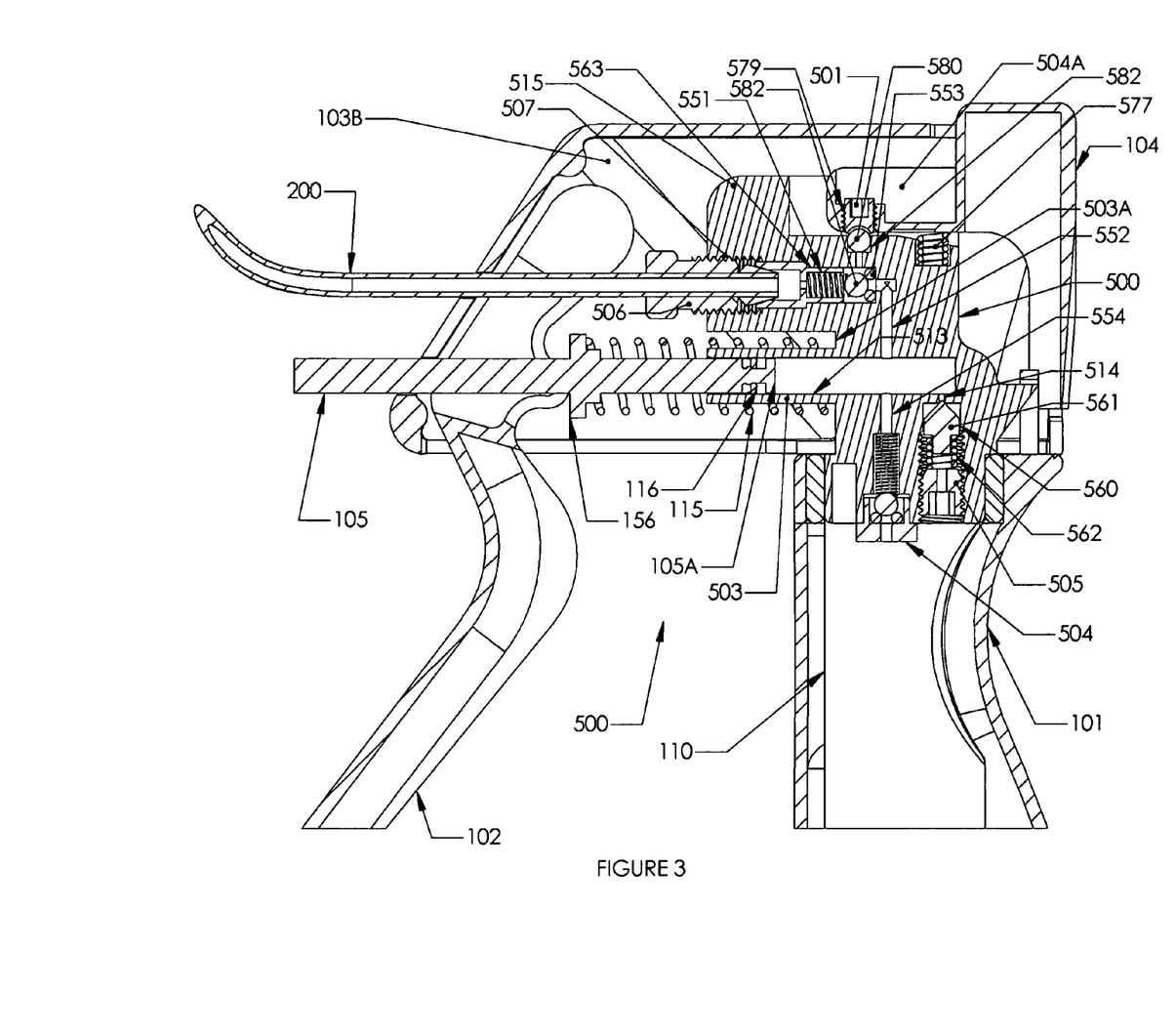
FIG. 3 is a sectional view of the control valve section of the manual pump part of the instant invention.

Referring now to FIG. 3, there is shown a partially sectional, partially broken away view of the assembled control valve mechanism body 500 of the manual pump 100 as shown in FIG. 2.

The trigger 102 is pivotally mounted to the inside of housing 103. The piston 105 passes through an aperture in the mid portion of trigger 102 and into cavity 513 in chamber 503.

The inner end 105A of piston 105 includes a groove therearound for receiving a suitable seal 116 such as an O-ring or the like. An appropriate abutment 156 (or shoulder) engages the inner surface of the trigger 102 and one end of spring 115. The spring 115, in this embodiment a coil spring, surrounds the inner portion of piston 105 and the outer surface of chamber 503. The spring is interposed between abutment 156 and the shoulder 503A of chamber 503 to spring-load the piston 105 and the trigger 102 in the outwardly position (i.e., to the left in FIG. 3).

An exit chamber 507 is connected to and communicates with conduit 200. A check valve 551 is provided in chamber 507 to control fluid flow from chamber 513 to chamber 507 via channel 552.

Check value 551 includes a ball 562 which is spring loaded by spring 563 in check valve 551 to seat against the inlet from channel 552 which is defined by an O-ring 553 or similar seal set.

In addition, chamber 555 is connected to and communicates from chamber 513 with container 110 via channel 554. Check valve 504 is provided in chamber 555 to control fluid flow between chamber 513 and container 110.

In operation, the trigger 102 is actuated by pulling toward the handle 101. The trigger pivots about the pins 112 in the hubs 113. In addition, the trigger 102 bears upon the shoulder 156 of piston 105 and pushes the piston inwardly against spring 115.

As piston 105 moves inwardly in chamber 513, the contents of chamber 513 (initially, air) is compressed and forces check valve 504 to remain closed while forcing check valve 551 open. Thus, the contents of chamber 513 passes through channel 552 and chamber 507 into conduit 200.

When the trigger 102 is released, the piston 105 is withdrawn from chamber 513 under force of spring 115. This action creates a vacuum in chamber 513 which draws the fluid from container 110 via check valve 504 and chamber 555.

Upon the next activation of trigger 102, piston 105 again forces the contents (now liquid) from chamber 513 into channel 552, through check valve 551 and into conduit 200 to apply pressure at the end thereof.

Relief valve 560 is connected between pressure chamber 513 and the container (reservoir) 110. The plug 561 is urged by spring 562 to block the outlet orifice 514 from chamber 513.

However, when the pressure in chamber 513 exceeds a predetermined level, the plug 561 is forced downwardly so that the contents of chamber 513 can flow through relief valve 560 into container 110. Thus, the pressure exerted on and by the contents of chamber 513 is limited and an over pressure condition in the system is avoided.

Similarly, the pressure release mechanism including actuator 104 is mounted at the upper rear portion of body 500. In particular, pins 504A on the actuator 104 are pivotally mounted in slots 575 in the pivot support which is formed about the chamber 506. Spring 577 is located in the pivot support 576, typically in a recess 578. Spring 577 is disposed behind the pivot pins 504 and slots 575 as so to apply an upward (closing) force in the actuator 104. The actuator 104 includes, typically, an opening 579 in the lower surface of the forward section relative to the pivot pins 504. The opening 579 is adapted to provide a seat for the check ball 580 as well as a passage for a set screw 581 which is adjustable in the passage relative to the actuator 104.

The check ball 580 is disposed in a recess 582 in the support 515 which recess communicates with chamber 507.

In operation, when a process of pumping has been terminated, the actuator 104 is pressed at the lower back end thereof. The actuator 104 pivots around pins 504 (against the force of spring 577). The check ball 580 is free to move upwardly (within the confines of recess 582) as determined by set screw 581, thereby unblocking the communication with chamber 507. The pressurized fluid (liquid) applied to chamber 507 via conduit 552 is immediately released through unblocked recess 582 wherein pressure in conduit 200 is immediately released and possible "run-on" at the output of the system is prevented.

When actuator 104 is released, spring 577 pivots the actuator to the closed position which returns check ball 580 to the blocking position in recess 582 where it remains under pressure of the actuator as determined by spring 577. The set screw 581 can provide "fine tuning" of the closure operation by check ball 580.

Figure 4:
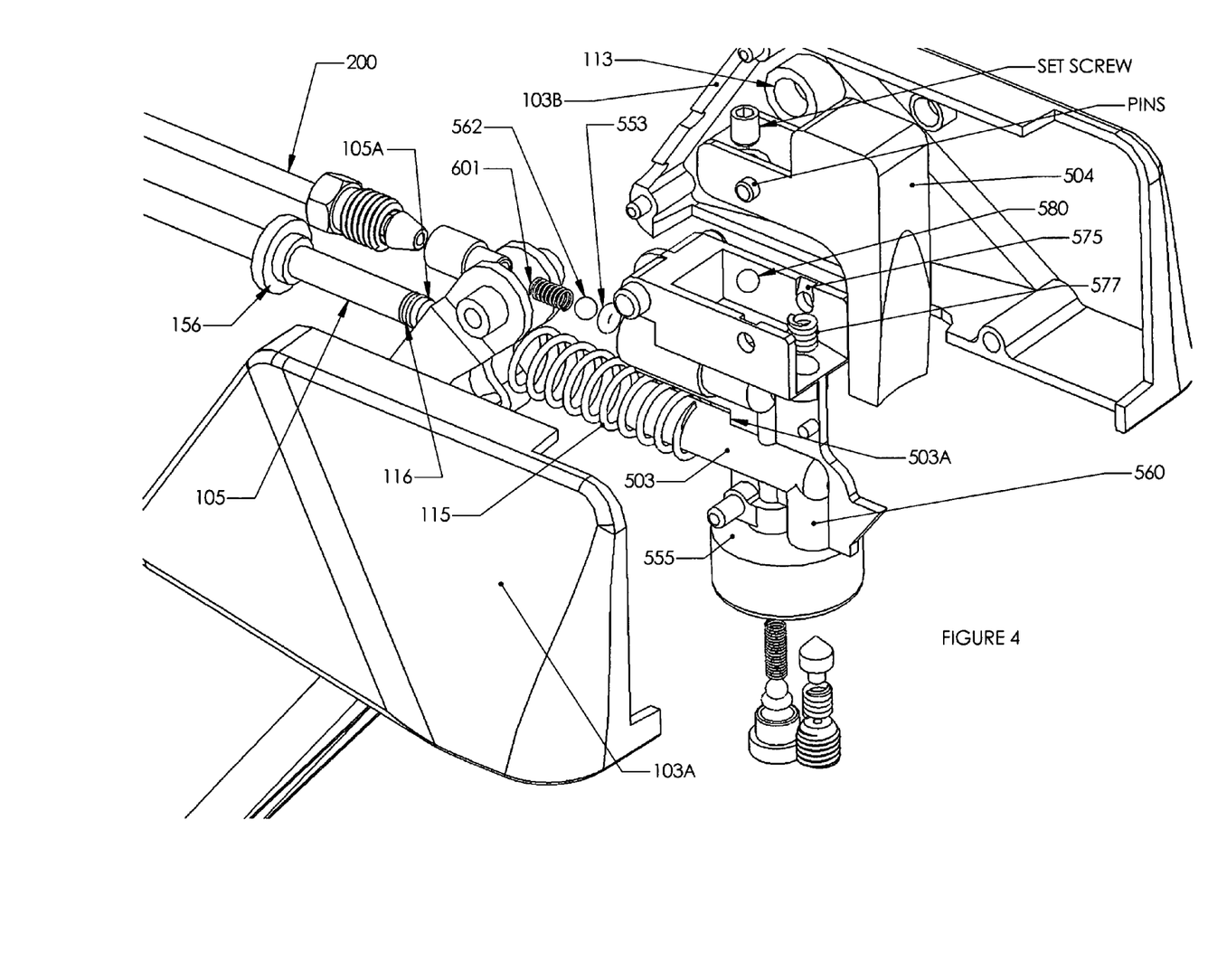
FIG. 4 is an enlarged, exploded perspective view of the control valve section of the manual pump part of the instant invention as shown in FIG. 3.

Referring now to FIG. 4, there is shown an enlarged, exploded view of a portion of the control valve section of body 500 of the system of the instant invention shown in FIGS. 2 and 3.

The pins 112 of trigger 102 are pivotally mounted to hubs 113 on the inside of housing 103 (sides 103A and 103B, respectively). The piston 105 passes through an aperture in the mid portion of trigger 102 (see FIG. 3) and into cavity 513 in chamber 503.

The inner end 105A of piston 105 includes a groove therearound for receiving a suitable seal 116 such as an O-ring or the like. An appropriate abutment (or shoulder) 156 (see FIG. 3) engages the inner surface of the trigger 102 and one end of spring 115 which surrounds the inner portion of piston 105 and the outer surface of chamber 503. The spring is interposed between abutment 156 and the shoulder 503A of chamber 503 to spring-load the piston 105 and the trigger 102 in the outwardly position (i.e., to the left in FIG. 4).

The exit chamber 507 is connected to and communicates with conduit 200. A check valve 551 is provided in chamber 507 to control fluid flow from chamber 513 to chamber 507 via channel 552.

Check value 551 includes a ball 562 which is spring loaded by spring 601 in check valve 551 to seat against the inlet from channel 552 which is defined by an O-ring 553 or similar seal set (see FIG. 3).

In addition, chamber 555 is connected to and communicates with container 110 via channel 554. Check valve 504 is provided in chamber 555 to control fluid flow between chamber 513 and container 110.

Chamber 560 is connected to and communicates with chamber 513 and container 110.

Once again, in operation, the trigger 102 is actuated by pulling toward the handle 101. The trigger pivots about the pins 112 in the hubs 113. In addition, the trigger 102 bears upon the abutment 156 of piston 105 and pushes the piston inwardly against spring 115.

As piston 105 moves inwardly in chamber 513, the contents of chamber 513 forces check valve 504 to remain closed while forcing check valve 551 open. Thus, the contents of chamber 513 passes through channel 552 and chamber 507 into conduit 200.

When the piston 105 is withdrawn from chamber 513, the trigger 102 is released, and creates a vacuum therein which draws the fluid from container 110 via check valve 504.

When trigger 102 is activated again, piston 105 again forces the contents (now liquids) from chamber 513 into channel 552, check valve 551 and into conduit 200 to apply pressure at the end thereof.

Relief valve 560 is connected between pressure chamber 513 and the reservoir 110. The plug 561 is urged by spring 562 to block the outlet orifice 514 from chamber 513.

Thus, when the pressure in chamber 513 exceeds a predetermined level, the plug 561 is forced downwardly so that the contents of chamber 513 can flow through relief valve 560 into container 110. Thus, the pressure exerted on and by the contents of chamber 513 is limited and an over pressure condition in the system is avoided.

Similarly, the pressure release mechanism including actuator 104 is mounted at the upper rear portion of body 500. In particular, pins 504 on the actuator 104 are pivotally mounted in slots 575 in the pivot support 576 which is formed about the chamber 506. Spring 577 is located in the pivot support 576, typically in a recess 578. Spring 577 is disposed behind the pivot pins 504 and slots 575 as so to apply an upward (closing) force in the actuator 104. The actuator 104 includes, typically, an opening 579 in the lower surface thereof in the forward section relative to the pivot pins 504. The opening 579 is adapted to provide a seat for the check ball 580 as well as a passage for a set screw 581 which is adjustable in the passage relative to the actuator 504.

The check ball 580 is disposed in a recess 582 (shown dashed) in the support 515 which recess communicates with chamber 507.

When a pumping process has been terminated, the actuator 104 is pressed at the lower back end thereof. The actuator 104 pivots around pins 504 against the force of spring 577, and the check ball 580 is free to move upwardly within recess 582 (as determined by set screw 581) thereby unblocking the communication with chamber 507. The pressurized liquid applied to chamber 507 via conduit 552 is immediately released through unblocked recess 582 wherein pressure in conduit 200 is immediately released an possible "run-on" at the output of the system is prevented.

When actuator 104 is released, spring 577 pivots the actuator to the closed position which returns check ball 580 to the blocking position in recess 582 where it remains under pressure of the actuator as determined by spring 577. The set screw 581 can provide "fine tuning" of the closure operation by check ball 580.

Figure 5:
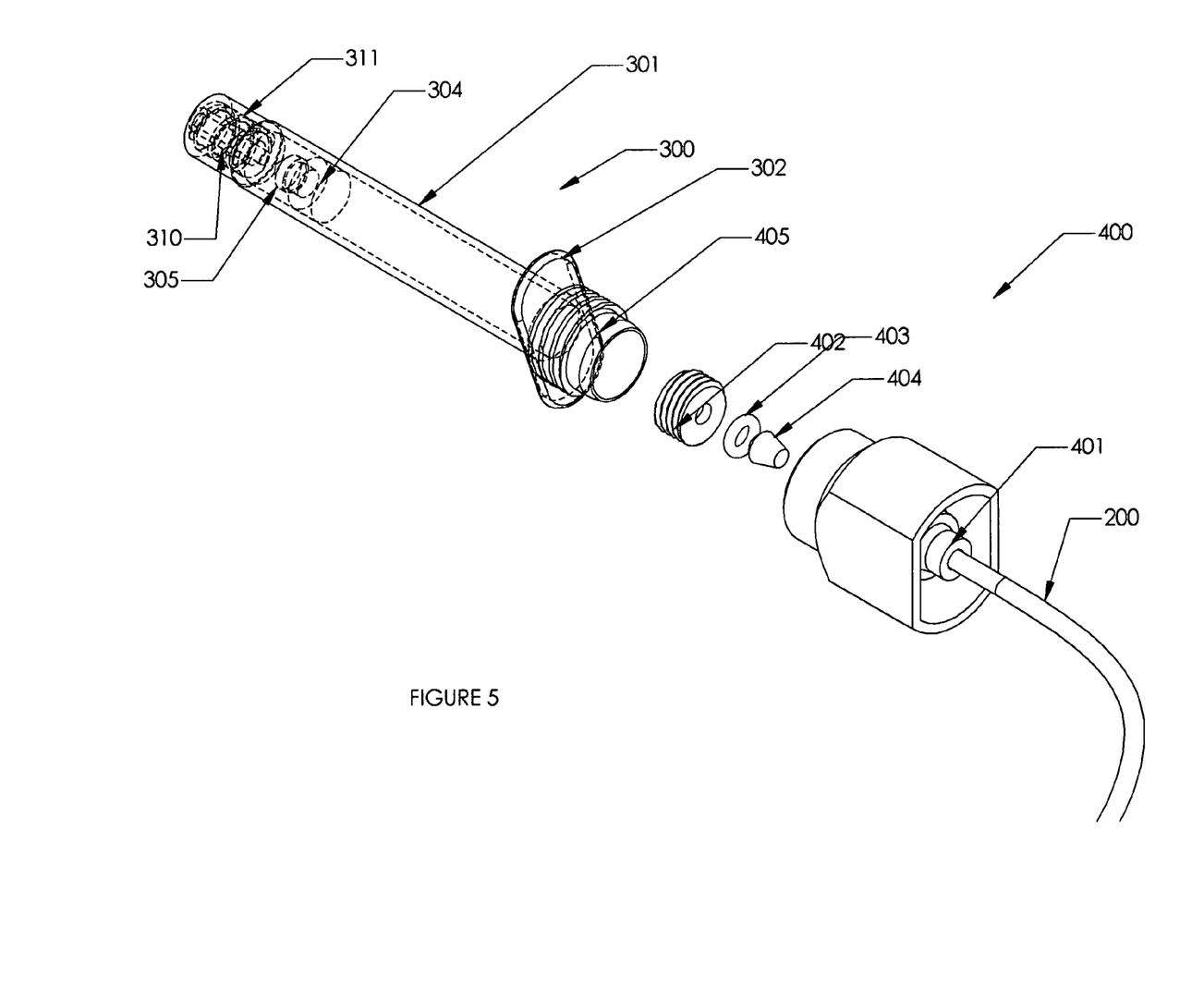
FIG. 5 is an enlarged, partially exploded view of the syringe and delivery portion of the instant invention.

Referring now to FIG. 5, there is shown an enlarged, partially exploded view of the connections of the syringe and delivery system of the instant invention. The conduit 200 is passed through an opening in a central support structure 401 in connector housing 400 and joined to a threaded connector 402 by an O-ring 403 and a ferrule 404. The interior surface of the central support structure 401 is threaded to selectively engage the outer threaded surface of connector 402 and to capture O-ring 403 to provide an internal seal.

For control purposes, the inner surface of the central support structure includes a sloped surface which engages the ferrule 404 and a shoulder which engages set screw 402 for proper seating of the seal.

In assembly, the conduit is passed through the central support structure 401, the ferrule 404, the O-ring 403 and the set screw 402. The set screw 402 is threaded into the threaded portion of support structure 401 to seal the ferrule and to compress the O-ring to secure the conduit in the housing 400 and to provide a seal therearound.

The housing 401 is also threadedly engaged with the threaded end 405 of syringe 301. The threaded end may be attached to or integrally formed with the syringe body 301. (The finger tabs 302 may be formed with the syringe body, if so desired.)

A plunger 304 fits snugly within the syringe body 301 and is attached to a seal 305 which prevents leakage around the plunger.

The outlet 310 of the syringe is a hollow cylinder or tube which communicates with the interior of the syringe. A conventional Luer connector 311 is formed at the end of the syringe and surrounds the outlet 310. The outlet 310 and the Luer connector 311 are adapted to engage, inter alia, a conventional Trocar instrument (not shown).

Figure 6:
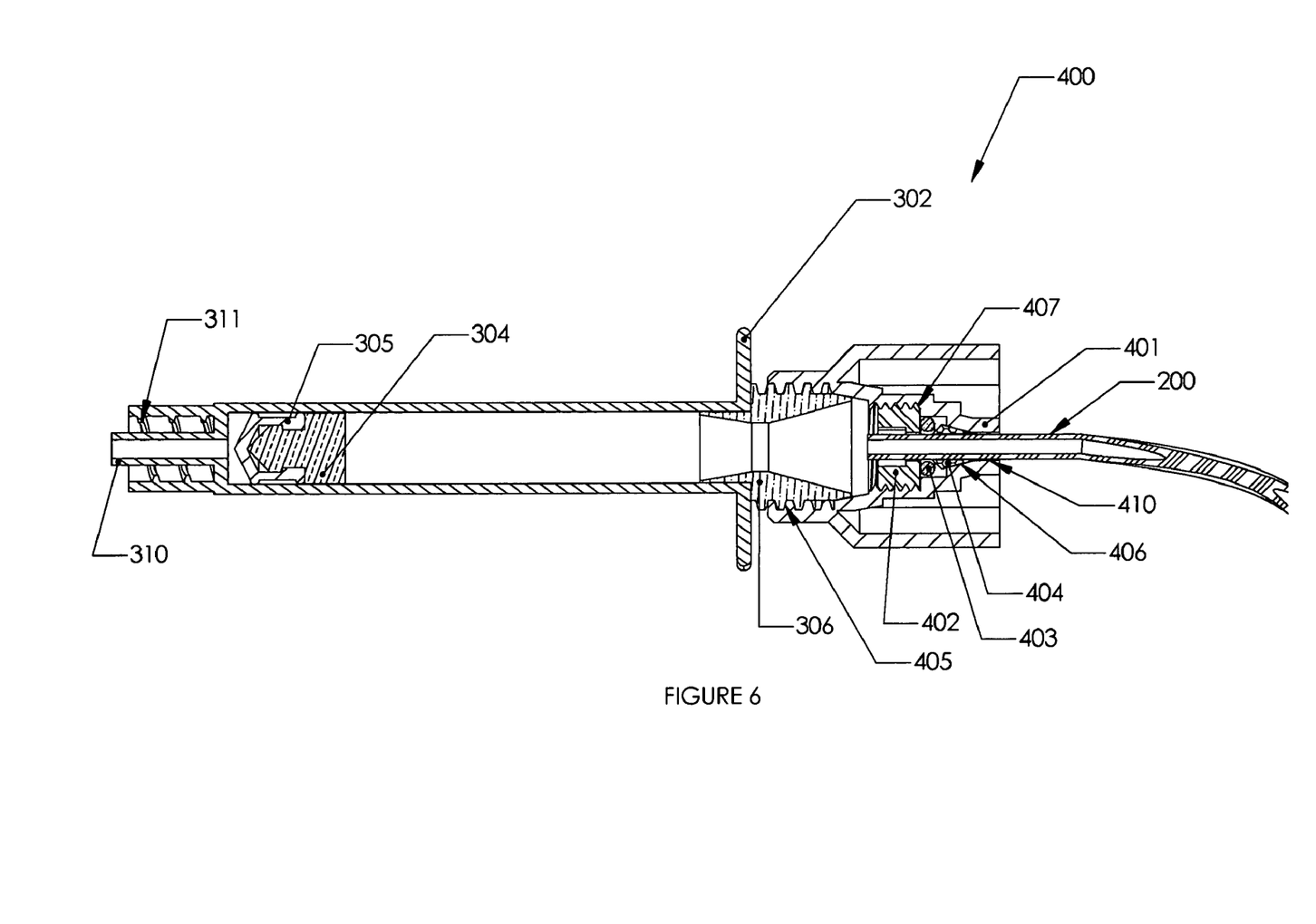
FIG. 6 is a cross-sectional view of the syringe and delivery portion of the instant invention.

Referring now to FIG. 6, there is shown a cross-sectional view of one embodiment of the connections of the syringe 301 and delivery system of the instant invention as shown in FIG. 5. The conduit 200 is passed through an opening 410 which is provided in a central support structure 401 portion of connector housing 400. Conduit 200 is joined to a threaded connector (or set screw) 402 by an O-ring 403 and a ferrule 404. A portion of the interior surface of the central support structure 401 is threaded to selectively engage the outer threaded surface of connector 402. A portion of the interior surface of support structure 401 is sloped to engage ferrule 404 to capture O-ring 403 to provide an internal seal for the connector 400. That is, the inner surface of the central support structure 401 includes a sloped surface 406 which engages the sloped surface of ferrule 404 and a shoulder 407 which engages set screw 402 for proper seating of the seal.

In assembly, the conduit 200 is passed through the central support structure 401, the ferrule 404, the O-ring 403 and the set screw 402. The set screw 402 is threaded into the threaded portion of support structure 401 to seal the ferrule and to compress the O-ring to secure the conduit in the housing 400 and to provide a seal therearound.

The housing 401 is also threadedly engaged with the threaded end 405 of syringe 300. The threaded end may be attached to or integrally formed with the syringe body 301.

Figure 7:
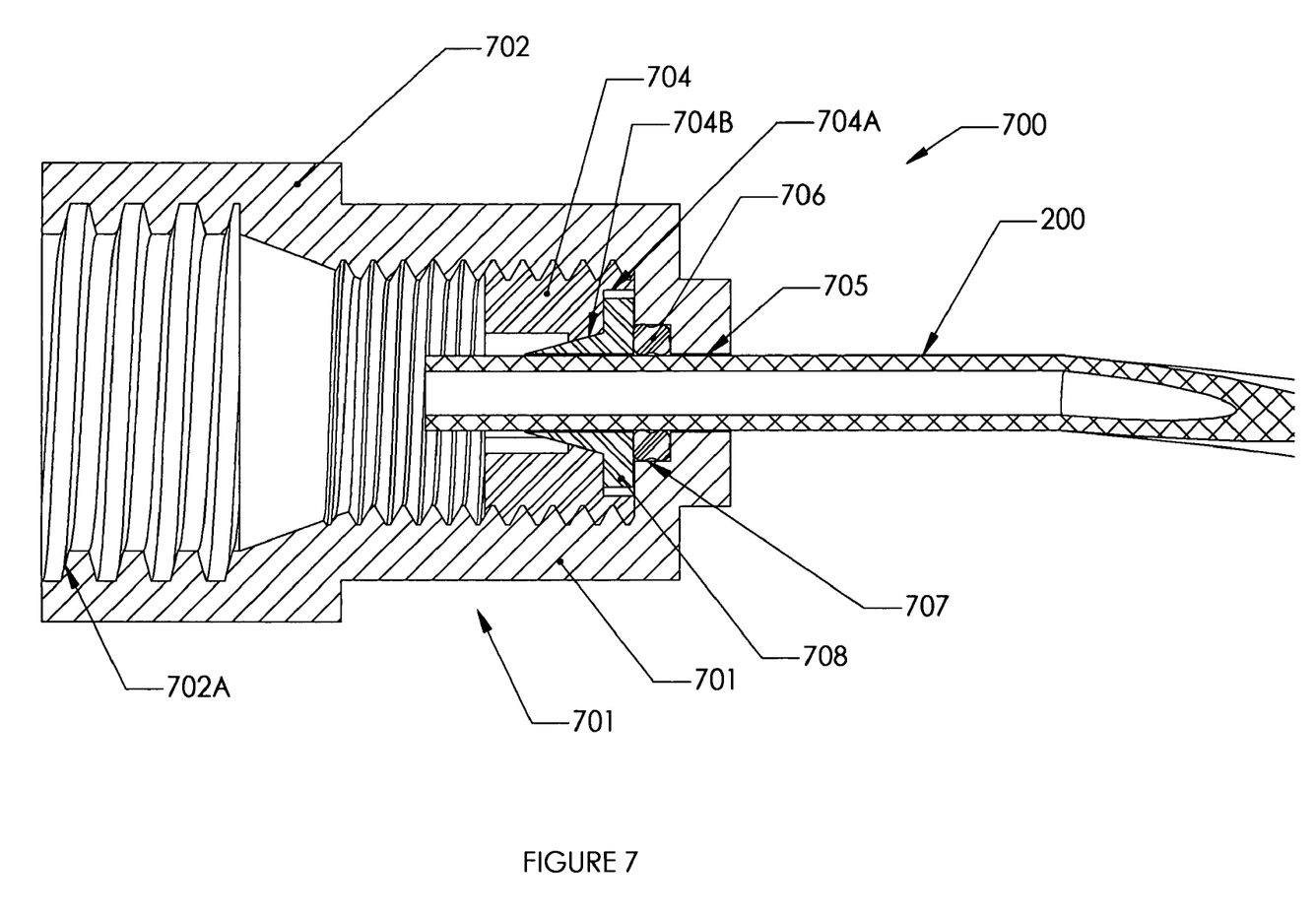
FIG. 7 is a partially broken away, partially cross-sectional view of an alternative connector construction.

Referring now to FIG. 7, there is shown a partially broken away, partially cross-sectional view of an alternative construction of the connector 700 of the instant system. The connector 700 includes connector housing 701 which, typically, comprises a knurled or faceted surface portion 702 and a cylindrical end 703. These components are deemed desirable but can be of other shapes, if so desired.

The interior surface 702A of the faceted portion 702 of the connector is threaded to receive and engage the threaded connector on the syringe 300.

The interior surface of the cylindrical end 703 is also threaded to receive and engage the set screw 704 which is selectively interacted with the connector housing 701. The set screw 704 includes a recess 704A at the inner end thereof as well as a tapered surface 704B surrounding the axial aperture through the recess 704A.

In assembly, the conduit 200 is inserted into the cylindrical end 703 of housing 701 via aperture 705 which is, preferably, a snug fit.

A suitable O-ring 706 is snugly engaged with conduit 200 and mounted in a receiving groove 707 in the interior end wall of housing 701. In a preferred embodiment, the O-ring 706 is a double O-ring for secure sealing around the conduit 200.

In this embodiment, the sleeve or ferrule 708 includes a tapered or conic end as well as a flat or washer-like end. The flat end abuts against the interior surface of cylindrical end 703 and retains O-ring 706 in the groove 707 when the set screw 704 is put in place and the tapered surface 704B wedges against the tapered or conic surface of the ferrule 707.

Thus, either connector 400 or 700 (or any suitable replacement) can be attached to the syringe. There are several advantages of the connector designs described above. For example, the connector 400 or 700 is capable of rotating around the conduit 200 without twisting or "kinking" the conduit 200 while maintaining a secure seal.

The connector 400 or 700 bleeds off any air which is present within the syringe when the system is connected together. The trapped air, if any, gathers inside the space inside the set screw 402 or 704, respectively. This air can escape around the conduit 200 as sealed by the O-ring 403 or 706, respectively.

When the air has escaped, the connector 400 or 700 seals against the liquid which is in the syringe 300 (i.e., the drive liquid) and prevents leakage at this juncture as discussed.

That is, a plunger 304 fits snugly within the syringe body 301 and is attached to a seal 305 which prevents leakage around the plunger. (See FIGS. 1 and 5)

The outlet 310 of the syringe is a hollow cylinder or tube which communicates with the interior of the syringe. A conventional threaded Luer connector 311 is formed at the end of the syringe and surrounds the outlet 310 as shown in FIG. 5.

In a typical operation, the pump mechanism 100 is assembled as shown in FIGS. 1 and 2 including a liquid such as a saline solution, purified water or the like container 110.

Substantially concurrently, the viscous material is placed into the syringe 301 in a suitable manner (see infra). The outlet connector 311 is connected to the application site. In one operation, the outlet connector 311 is a Luer connector which is threaded to the end of a Trocar instrument which has been inserted into place. The plunger 304 and seal 305 are placed into the syringe 301 in proximity to the viscous material. The inlet connector 306 of the syringe is threadedly attached to the coupler housing 400 (again a Luer fitting can be utilized).

The apparatus is now assembled and ready for operation. By activating the trigger 102, liquid is drawn out of container 110 and forced through conduit 200 via the connector 400 or 700 into syringe 301 to exert force against plunger 304. As the plunger 304 (with seal 305) is forced through the syringe 301, the viscous material in the syringe is forced out through the outlet connector 310 into the operational tool or to the application site.

As described supra, the several check valves in the valve portion 500 permit the liquid to flow into the conduit 200 under controlled pressure but not in the reverse direction.

When the application of the viscous material is completed, the pressure release valve 104 is activated to immediately relieve the pressure on the liquid in the conduit 200 and, thus, on the viscous material in the syringe. This quick release of pressure prevents "run-on" of viscous material from syringe 301 into the application site.

Thus, there is shown and described a unique design and concept of a manual pump mechanism and delivery system for viscous materials. While this description is directed to particular embodiments, it is understood that those skilled in the art may conceive modifications and/or variations to the specific embodiments shown and described herein. Any such modifications or variations which within the purview of this description are intended to be included therein as well. It is understood that the description herein is intended to be illustrative only and is not intended to be limitative. Rather, the scope of the invention described herein is limited only by the claims appended hereto.

The invention claimed is:

1. A pumping system comprising:
a source of fluid for selective pressurization;
a hydraulic mechanism structurally configured to apply high pressure to said fluid, the hydraulic mechanism comprising a trigger pivotally mounted within a housing, the housing including valves mounted therein that control the movement of fluid and also including a manually operable actuator at a distal end of the housing allowing manual pressure release by one hand of a user while holding the housing in the same one hand, the manually operable actuator selectively releasing pressure on said fluid within a conduit by releasing at least a portion of said fluid out of the conduit and external to the fluid source;

the conduit selectively carrying said fluid from said source when said fluid is pressurized, the conduit extending from a proximal end of the housing that is substantially opposite of the distal end of the housing; and a container of a viscous material connected by a connector means to said conduit to receive pressurized fluid from said conduit to selectively force said viscous material from said container, wherein said connector means rotates about said conduit to permit selective bleeding of air from said container, wherein said connector means includes a hollow housing for receiving an end of said conduit through an axial opening therein; a set screw threadedly engaged with the interior of said hollow housing and surrounding said end of said conduit; seal means surrounding said end of said conduit; and ferrule means surrounding said end of said conduit, said set screw adapted to force said ferrule means and said seal means into contact with the interior of said hollow housing to provide a seal around said conduit in said hollow housing, wherein the valves include first and second automatic pressure valves such that a pressure chamber for said liquid is formed between said first and second automatic pressure valves, the first automatic pressure valve operable to allow said fluid to leave said pressure chamber and flow to said container when said pressurized fluid exceeds a first predetermined pressure threshold magnitude, the second automatic pressure valve operable to return pressurized fluid to said source when said pressurized fluid exceeds a second predetermined pressure threshold magnitude, wherein said second predetermined threshold is greater than said first predetermined threshold.

2. The system recited in claim 1, wherein the conduit is a flexible tube.

3. The system recited in claim 1, wherein said source of fluid comprises a reservoir for storing said fluid.

4. The system recited in claim 1 wherein said fluid is an incompressible liquid.

5. The system of claim 1, where the system operates at moderate to high pressures ranging from at least about 1,000 psi to 2,000 psi.

6. The system of claim 1 wherein, said conduit is long enough to permit a user/surgeon to be outside of a radiation field of a patient being imaged.

7. The pumping system of claim 6, further comprising valves within the housing for controlling the movement of said fluid from said source of fluid through said conduit whereby and, a connector which is capable of rotating around the conduit and bleeding off of any air present when the system is operating, both manually and automatically.

8. A hand-held pumping system comprising:
a source of fluid for selective pressurization;
a housing means for containing the source of fluid;
a mechanism for applying pressure to said fluid;
a flexible conduit for selectively carrying said fluid from said source when said fluid is pressurized, said flexible conduit having an inlet end operative to receive the fluid, and an outlet end for discharging the received fluid, said flexible conduit extending from a proximal end of said housing means that is substantially opposite of a distal end of said housing means;

a container of a viscous material connected by a connector means to said outlet end of said conduit said conduit to receive pressurized fluid from said conduit to selectively force said viscous material from said container, wherein said connector means rotates about said conduit to permit selective bleeding of air from said container, wherein said connector means includes a hollow housing for receiving an end of said conduit through an axial opening therein; a set screw threadedly engaged with the interior of said hollow housing and surrounding said end of said conduit; seal means surrounding said end of said conduit; and ferrule means surrounding said end of said conduit, said set screw adapted to force said ferrule means and said seal means into contact with the interior of said hollow housing to provide a seal around said conduit in said hollow housing;

a pressure release mechanism connected to said distal end of said housing means for selectively relieving pressure from said fluid in said conduit by releasing at least a portion of said fluid out of the conduit and external to the fluid source; and first and second automatic pressure valves connected to said housing such that a pressure chamber for said liquid is formed between said first and second automatic pressure valves, the first automatic pressure valve operable to allow said fluid to leave said pressure chamber and flow through said inlet of flexible conduit when said pressurized fluid exceeds a first predetermined pressure threshold magnitude, the second automatic pressure valve operable to return pressurized fluid to said source when said pressurized fluid exceeds a second predetermined pressure threshold magnitude, wherein said second predetermined threshold is greater than said first predetermined threshold.

9. The system recited in claim 8 including handle means for supporting said source of fluid.

10. The system recited in claim 9 wherein said mechanism for applying pressure to said fluid comprises, trigger means mounted to said handle means for selectively applying pressure to said fluid in said source of fluid.

11. The system recited in claim 10 including:
housing means formed with said handle means; and
wherein the first and second automatic pressure valves are mounted in said housing means for controlling the movement of said fluid from said source of fluid through said conduit.

12. The system recited in claim 8 including:
wherein the first and second automatic pressure valves are mounted in said housing means for controlling the movement of said fluid from said source of fluid through said conduit.

13. The system recited in claim 8, wherein the pressure release mechanism comprises a valve, and wherein the pressure release mechanism is pivotally rotatable about a pin connection to release the valve.

14. The system recited in claim 8, comprising a relief valve between the source of fluid and the pressure chamber for automatically releasing fluid to the pressure chamber when the pressure exceeds a third predetermined pressure threshold magnitude within the source of fluid, wherein the pressure release mechanism is disposed to release pressure from the conduit and wherein the relief valve is disposed to release pressure from the fluid source pressurizable by the trigger means.

* * * * *